(12) United States Patent
Mogna

(10) Patent No.: US 11,026,922 B2
(45) Date of Patent: Jun. 8, 2021

(54) COMPOSITIONS COMPRISING MELATONIN AND FLAVONOIDS FOR USE IN THE TREATMENT OF TUMOURS RESISTANT TO CHEMOTHERAPY

(71) Applicant: PROBIOTICAL S.P.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 756 days.

(21) Appl. No.: 15/326,627

(22) PCT Filed: Mar. 5, 2015

(86) PCT No.: PCT/IB2015/000284
§ 371 (c)(1),
(2) Date: Jan. 16, 2017

(87) PCT Pub. No.: WO2016/009256
PCT Pub. Date: Jan. 21, 2016

(65) Prior Publication Data
US 2017/0209416 A1    Jul. 27, 2017

(30) Foreign Application Priority Data
Jul. 17, 2014  (IT) .......................... MI2014A001308

(51) Int. Cl.
| A61K 31/4045 | (2006.01) |
| A61K 45/06 | (2006.01) |
| A61K 31/675 | (2006.01) |
| A61K 31/7048 | (2006.01) |
| A61K 36/28 | (2006.01) |
| A61K 36/29 | (2006.01) |
| A61K 36/66 | (2006.01) |
| A61P 35/00 | (2006.01) |
| A61P 35/04 | (2006.01) |

(52) U.S. Cl.
CPC ........ *A61K 31/4045* (2013.01); *A61K 31/675* (2013.01); *A61K 31/7048* (2013.01); *A61K 36/28* (2013.01); *A61K 36/29* (2013.01); *A61K 36/66* (2013.01); *A61K 45/06* (2013.01); *A61P 35/00* (2018.01); *A61P 35/04* (2018.01); *A61K 2236/17* (2013.01); *A61K 2236/31* (2013.01); *A61K 2236/333* (2013.01); *A61K 2236/53* (2013.01)

(58) Field of Classification Search
CPC ........ A61K 36/28; A61K 36/66; A61K 36/29; A61K 36/9066; A61K 2300/00; A61K 31/4045; A61K 31/675; A61K 31/7048; A61K 2236/17; A61K 2236/31; A61K 2236/333; A61K 2236/53; A61K 45/06; A61K 31/365; A61K 31/4375; A61K 31/4741; A61K 31/4748; A61K 31/519; A61P 35/00; A61P 35/04; A61P 43/00

USPC .............................. 424/742, 749, 756, 777
See application file for complete search history.

(56) References Cited

U.S. PATENT DOCUMENTS

| 6,426,351 | B1 * | 7/2002 | Weichselbaum | A61K 31/335 |
|  |  |  |  | 514/280 |
| 9,757,405 | B2 | 9/2017 | Frascini et al. | |
| 10,195,219 | B2 * | 2/2019 | Bent | A61K 45/06 |
| 2011/0182943 | A1 | 7/2011 | Kanwar et al. | |
| 2013/0045179 | A1 * | 2/2013 | Ciustea | A61K 45/06 |
|  |  |  |  | 424/85.1 |
| 2014/0141082 | A1 | 5/2014 | Gao | |
| 2016/0213698 | A1 | 7/2016 | Frascini et al. | |
| 2018/0064774 | A1 | 3/2018 | Mogna | |

FOREIGN PATENT DOCUMENTS

| CN | 1560265 A | 1/2005 |
| CN | 1911951 A | 2/2007 |
| CN | 103608005 A | 2/2014 |
| EP | 1656939 A1 | 5/2006 |
| EP | 2119434 A1 | 11/2009 |
| JP | 2005529123 A | 9/2005 |
| WO | 200178783 A2 | 10/2001 |
| WO | 03/090681 A3 | 11/2003 |
| WO | 2006/032380 A1 | 3/2006 |
| WO | 2008/108647 A2 | 9/2008 |
| WO | 2010/001391 A1 | 1/2010 |
| WO | 2012/141575 A1 | 10/2012 |
| WO | 2015/036875 A1 | 3/2015 |
| WO | 2016/139625 A1 | 9/2016 |

OTHER PUBLICATIONS

Nazari et al. "Inactivation of Nuclear Factor-κB by citrus flavanone hesperidin contributes to apoptosis and chemo-senitizing effexct in Ramos cells", European Journal of Pharmacology 650, 526-533 (Year: 2011).*
Yun et al. "Melatonin Sensitizes H1975 Non-Small-Cell Lung Cancer Cells Harboring a T790M-Targeted Epidermal Growth Factor Receptor Mutation to the Tyrosine Kinase Inhibitor Gefitinib", Cellular Physiology and Biochemistry, 2014: 34:865-872 (Year: 2014).*
Yao et al. "Arctigenin Enhances Chemosensitivity of Cancer Cells to Cisplatin Through Inhibition of STAT3 Signaling Pathway", Journal of Cellular Biochemistry, 112:2837-2849. (Year: 2011).*
Martin et al. "Melatonin-induced methylatin of the ABCG2/BCRP romoter as a novel mechanism to overcome multidrug resistance in brain tumour stem cells", British Hournal of Cancer, 2013, 108, 2005-2012. (Year: 2013).*

(Continued)

*Primary Examiner* — Aaron J Kosar
(74) *Attorney, Agent, or Firm* — Steinfl + Bruno LLP

(57) ABSTRACT

Compositions having at least one flavonoid of natural or synthetic origin in association with melatonin to increase the effectiveness of chemotherapeutic treatments used in human and veterinary medicine for the treatment of tumours are described. The compositions are in particular for the treatment of tumours resistant to the chemotherapeutic agents currently in use. The at least one flavonoid is selected from rutin, oxerutin, diosmin and hesperidin, preferably rutin.

20 Claims, 2 Drawing Sheets

(56) References Cited

OTHER PUBLICATIONS

Figure 1:
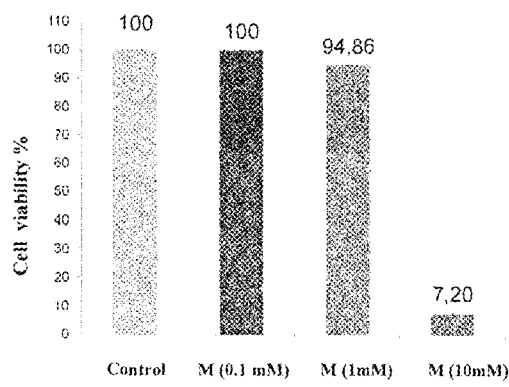

Altgelt, Johanna "Breast Cancer, Chemotherapy, & Antioxidants", online (retrieved Feb. 2021 from <URL:pinestreetfoundation.org/breast-cancer-chemotherapy-antioxidants/>), Pine Street Foundation, Sep. 23, 2007, 17 pages. (Year: 2007).*

Yi C, et al. "Melatonin Enhances the Anti-Tumor Effect of Fisetin by Inhibiting COX-2/iNOS and NF-κB/p300 Signaling Pathways" PLoS ONE, 2014, 9(7): e99943, 11pp.; doi:10.1371/journal.pone.0099943 (Year: 2014).*

Kashif M, et al "Cytotoxic and antioxidant properties of phenolic compounds from Tagetes patula flower" Pharmaceutical Biology, Dec. 24, 2014, 53(5), pp. 672-681, doi: 10.3109/13880209.2014.936471. (Year: 2014).*

International Search Report and Written Opinion for International Application No. PCT/IB2015/000284 filed Mar. 5, 2015 on behalf of Brobiotical S.P.A. dated Jul. 10, 2015. 15 pages.

Bourogaa et al. "Hammada scoparia flavonoids and rutin kill adherent and chemoresistant leukemic cells" Leukemia Research, Aug. 2011, 35(8); pp. 1093-1101.

Duvoix et al. "Effect of chemopreventive agents on glutathione S-transferase P1-1 gene expression mechanisms via activating protein 1 and nuclear factor kappaB inhibition" Biochemical Pharmacology, Sep. 2004, 68(6), pp. 1101-1111—Abstract Only.

Fojo et al. "Mechanisms of Resistance to PARP Inhibitors—Three and Counting" Cancer Discovery, Jan. 2013, 3(1); pp. 20-23.

Guardia et al. "Anti-inflammatory properties of plant flavonoids. Effects of rutin, quercetin and hesperidin on adjuvant arthritis in rat" Il Farmaco, 2001, 56, pp. 683-687.

Hanachi et al. "Cytotoxic Effect of Berberis vulgaris Fruit Extract on the Proliferation of Human Liver Cancer Cell Line (HepG2) and its Antioxidant Properties" International Journal of Cancer Research, 2006, 2(1), pp. 1-9.

Jung et al. "Anti-asthmatic action of quercetin and rutin in conscious guinea-pigs challenged with aerosolized ovalbumin" Arch. Pharm. Res., Dec. 2007, 30(12), pp. 1599-1607—Abstract Only.

Luo et al. "Inhibition of Cell Growth and VEGF Expression in Ovarian Cancer Cells by Flavonoids" Nutrition and Cancer, 2008, 60(6), pp. 800-809.

Mani et al "Insilico Analysis on the Effect of Rutin Bioflavonoid and Chemotherapeutic Drug Cyclophosphamide on Nuclear Factor Kappa-B Protein Expression" International Journal of Pharma and Bio Sciences, Jan. 2014, 5(1); pp. 560-569.

Metodiewa et al. "Evidence for Antiradical and Antioxidant Properties of Four Biologically Active N,N-Diethylaminoethyl Ethers of Flavanone Oximes: A Comparison with Natural Polyphenolic Flavonoid (Rutin) Action" Biochemistry and Molecular Biology International, Apr. 1997, 41(5), pp. 1067-1075.

Navarro-Nunez et al. "Apigenin Inhibits Platelet Adhesion and Thrombus Formation and Synergizes with Aspirin in the Suppression of the Arachidonic Acid Pathway" Journal of Agricultural and Food Chemistry, 2008, 56, pp. 2970-2976.

Takasaki et al. "Anti-tumor-promoting activity of lignans from the aerial part of Saussurea medusa" Cancer Letters, Sep. 2000, 158(1), pp. 53-59—Abstract Only.

Tang et al. "Recent Development of Antitumor Agents from Chinese Herbal Medicines; Part I. Low Molecular Compounds" Planta Medica, 2003, 69(2), pp. 97-108.

Yarnell et al. "Can Botanicals Reduce Multidrug Resistance in Cancer?" Alternative and Complementary Therapies, Jul. 2004, 8(6), pp. 336-340—1$^{st}$ Page Only.

Yun et al. "Melatonin Sensitizes H1975 Non-Small-Cell Lung Cancer Cells Harboring a T790M-Targeted Epidermal Growth Factor Receptor Mutation to the Tyrosine Kinase Inhibitor Gefitinib" Cellular Physiology and Biochemistry, Jan. 2014, 34(3); pp. 865-872.

Italian Search Report and Written Opinion for Italian Patent Application No. ITMI20141308 filed Jul. 17, 2014 on behalf of Probiotical S.P.A. dated Dec. 10, 2014. 7 pages (Italian original + English translation).

International Preliminary Report on Patentability for PCT/IB2015/000284 filed Mar. 5, 2015 on behalf of Probiotical S.P.A. dated Jan. 26, 2017. 10 pages.

Di Bella G. et al., The Di Bella Method (DBM) in the treatment of prostate cancer: a preliminary retrospective study of 16 patients and a review of the literature// Neuro Endocrin Lett., 2013, 34(6): 523-528, PMID: 24378460.

Gambashidze K. et al., Antitumor and adjuvant effects of phagelysates of E. coli in mice with Enrlich carcinoma//Exp. Oncol. Jul. 2012, 34(2): 107-111, PMID: 23013762.

Office Action for Russian Application No. 2017102705/15(004708) filed on Mar. 5, 2015 on behalf of Probiotical S.P.A., IT. dated Jul. 27, 2018. 18 pages (Russian + English translation).

Park SY et al., Sanguinarine inhibits invasiveness and the MMP-9 and COX-2 expression in TPA-induced breast cancer cells by inducing HO-1 expression//Oncol Rep., Jan. 2014, 31(1): 497-504, PMID: 24220687.

Raza H. et al., Alterations in mitochondrial respiratory functions, redox metabolism and apoptosis by oxidant 4-hydroxynonenal and antioxidants curcumin and melatonin in PC12 cells//Toxicol Appl Pharmacol., Jan. 15, 2008; 226(2): 161-168, PMID: 17935746.

Search Report for Russian Application No. 2017102705/15(004708) filed on Mar. 5, 2015 on behalf of Probiotical S.P.A., IT. dated Jul. 27, 2018. 5 pages (Russian + English translation).

Office Action for Japanese patent application No. JP 2017-502689, dated Jan. 7, 2020, 6 pages (with English translation).

Alonso Castro, et al., "Rutin exerts autitumor effects on nude mice bearing sw480 tumor", Archives of Medical Research 44, 2013, 346-351.

Cutando, et al., "Role of Melatonin in Cancer Treatment", Anticancer Research , 32: 2747-2753 (2012).

Japanese Office Action Application No. 2017-502689 dated Jan. 8, 2019 for applicant Probiotical S.P.A ,dated Jan. 8, 2019. 11 pages. (Original + English translation).

Jung, et al., "Melatonin in Cancer Management: Progress and Promise", Cancer Res, 2006, 66: (20), 9789-9793, Oct. 15, 2006.

Remington's Pharmaceutical Science, John M. Hoovered., 18th ed., 1990, Mack Publishing.

Srinivasan, et al, "Therapeutic Actions of Melatonin in Cancer: Possible Mechanisms", Integrative cancer therapies,2008, 7(3), 189-203.

Goodhart, G. et al. "Review Article: Pharmaceutical Sciences—1975: Literature Review of Pharmaceutics II", Journal of Pharmaceutical Sciences, Aug. 1976, vol. 65, No. 8, pp. 1101-1139. Preview 1 page.

Ahmad et al. "Differential Antiproliferative and Apoptotic Response of Sanguinarine for Cancer Cells versus Normal Cells" Clinical Cancer Research, American Association for Cancer Research. Apr. 2000. vol. 6. pp. 1524-1528. 5 pages.

Awale et al. "Identification of Arctogenin as an Antitumor Agent Having the Ability to Eliminate the Tolerance of Cancer Cells to Nutrient Starvation" Cancer Research, American Association for Cancer Research. Feb. 1, 2006. vol. 66, No. 3. pp. 1751-1757. 7 pages.

Chinese Office Action and Search Report for CN Appl. No. 2016800130286 filed on Mar. 4, 2016 on behalf of Probiotical S.P.A. dated Apr. 24, 2020. Plus English translation. 21 pages.

Communication pursuant to Article 94(3) received for EP App. No. 16718006.6 filed on Mar. 4, 2016 on behalf of Probiotical S.P.A. dated Feb. 12, 2020. 7 pages.

El-Readi et al. "Inhibition of P-glycoprotein activity by limonin and other secondary metabolites from Citrus species in human colon and leukaemia cell lines" European Journal of Pharmacology, Elsevier. 2010. vol. 626. pp. 139-145. 7 pages.

Febriansah et al. "Hesperidin as a preventive resistance agent in MCF-7 breast cancer cells line resistance to doxorubicin" Asian Pacific Journal of Tropical Biomedicine, Elsevier. 2014. vol. 4, No. 3, pp. 228-233. 6 pages.

Final Office Action for U.S. Appl. No. 15/555,920, filed Sep. 5, 2017 on behalf of Probiotical S.P.A. dated Nov. 19, 2019. 9 pages.

(56) References Cited

OTHER PUBLICATIONS

Gautam R. et al. "Rutin Attenuates Intestinal Toxicity Induced by Methotrexate Linked with Antioxidative and Anti inflammatory Effects". BMC Complementary & Alternative Medicine 16:99, pp. 1-6, 2016. (Year: 2016).
Hirose et al. "Effects of arctiin on PhIP-induced mammary, colon and pancreatic carcinogenesis in female Sprague-Dawley rats and MelQx-induced hepatocarcinogenesis in male F344 rats" Cancer Letters, Elsevier. 2000. vol. 155. pp. 79-88. 10 pages.
Indian Office Action for IN Application No. 201747032728 filed on Sep. 15, 2017 on behalf of Probiotical S.P.A. dated Jul. 13, 2020. 7 pages. Hindi and English.
International Preliminary Report on Patentability for International Application No. PCT/IB2014/063187, filed on Jul. 17, 2014, on behalf of Probiotical S.P.A. dated Mar. 15, 2016. 5 pages.
International Preliminary Report on Patentability for International Application No. PCT/IB2016/051216, filed on Mar. 4, 2016, on behalf of Probiotical S.P.A. dated Sep. 5, 2017. 7 pages.
International Search Report and Written Opinion for International Application No. PCT/IB2014/063187, filed on Jul. 17, 2014, on behalf of Probiotical S.P.A. dated Dec. 18, 2014. 7 pages.
International Search Report and Written Opinion for International Application No. PCT/IB2016/051216, filed on Mar. 4, 2016, on behalf of Probiotical S.P.A. dated Jun. 2, 2016. 11 pages.
Italian Application MI2014A001308 filed on behalf of Probiotical S.P.A./ Mogna. Filed on Jul. 17, 2014. Made available under the PCT on Feb. 8, 2016. Italian with English translation. 39 pages.
Italian priority Application No. MI2014A001308 filed on Jul. 17, 2014 on behalf of Probiotical S.P.A. Certified English translation dated Feb. 7, 2020. (19 pages).
Jantova et al. "Berberine induces apoptosis through a mitochondrial-caspase pathway in human promonocytic U937 cells" Toxicology in Vitro, Elsevier. 2007. vol. 21. pp. 25-31. 7 pages.
Japanese Office Action for Japanese Patent Application No. 2017-546598 on behalf of Probiotical S.P.A dated Jan. 7, 2020, 5 pages. Japanese + English summary.
Malikova et al. "The effect of chelerythrine on cell growth, apoptosis, and cell cycle in human normal and cancer cells in comparison with sanguinarine" Cell Biology and Toxicology, Springer. 2006. vol. 22. pp. 439-453. 15 pages.
Mani et al. "Insilico Analysis on the Effect of Rutin Bioflavonoid and Chemotherapeutic Drug Cyclophosphamide on Nuclear Factor Kappa-B Protein Expression" International Journal of Pharma and Bio Sciences, Ubijournal. Jan. 2014. vol. 5, No. 1. pp. 560-569. 10 pages.
Lissoni P., et al., "Decreased Toxicity and Increased Efficacy of Cancer Chemotherapy Using the Pineal Hormone Melatonin in Metastatic Solid Tumour Patients with Poor Clinical Status," European J of Cancer 35(12)1688-1692, 1999. 5 pages.
Non-Final Office Action for U.S. Appl. No. 14/917,939, filed Mar. 9, 2016, on behalf of Probiotical S.P.A. dated Jan. 12, 2017. 17 pages.
Non-Final Office Action for U.S. Appl. No. 15/555,920, filed Sep. 5, 2017 on behalf of Probiotical S.P.A. dated May 1, 2020. 9 pages.
Non-Final Office Action for U.S. Appl. No. 15/555,920, filed Sep. 5, 2017 on behalf of Probiotical S.p.A dated May 2, 2019. 15 pages.
Notice of Allowance for U.S. Appl. No. 15/555,920, filed Sep. 5, 2017 on behalf of Probiotical S.P.A. dated Oct. 9, 2020. 14 pages.
Notice of Allowance for U.S. Appl. No. 14/917,939, filed Mar. 9, 2016, on behalf of Probiotical S.P.A. dated Jul. 3, 2017. 10 pages.
Office Action (Reasons for Refusal) for Japanese application No. 2017-502689 filed in the name of Probiotical S.P.A. dated Sep. 1, 2020. 5 pages. Original and English translation.

Potdar et al. "Phyto-chemical and pharmacological applications of Berberis aristata" Fitoterapia, Elsevier. 2012. vol. 83. pp. 817-830. 14 pages.
Restriction Requirement for U.S. Appl. No. 15/555,920, filed Sep. 5, 2017 on behalf of Probiotical S.P.A. dated Oct. 22, 2018. 9 pages.
Russian Office Action for RU Application No. 2017132516 filed on Mar. 4, 2016 filed on behalf of Probiotical S.P.A. dated Mar. 11, 2020. Original + English Translation. 13 pages.
Russian Office Action for RU application No. 2017132516 filed on Mar. 4, 2016 on behalf of Probiotical S.P.A. dated Sep. 2, 2019. Russian & English Trans. 16 pages.
Russian Office Action for RU2017132516 filed on Mar. 4, 2016 in the name of Probiotical S.p.A., IT. dated Jul. 23, 2020. Original+ Eng. 16 pages.
Russian Search Report for RU application No. 2017132516 filed on Mar. 4, 2016 on behalf of Probiotical S.P.A. dated Sep. 2, 2019. Russian& English Trans. 4 pages.
Tamaki et al. "Inhibitory Effects of Herbal Extracts on Breast Cancer Resistance Protein (BCRP) and Structure-Inhibitory Potency Relationship of Isoflavonoids" Drug Metabolism and Pharmacokinetics, Elsevier. 2010. vol. 25, No. 2. pp. 170-179. 10 pages.
Wang et al. "Suppression of growth, migration and invasion of highly-metastatic human breast cancer cells by berbamine and its molecular mechanisms of action" Molecular Cancer, BioMed Central Ltd. 2009. vol. 8, No. 81. 15 pages.
Webster et al. "Protective effect of rutin, a flavonol glycoside, on the carcinogen-induced DNA damage and repair enzymes in rats" Cancer Letters, Elsevier. 1996. vol. 109. pp. 185-191. 7 pages.
Communication pursuant to Article 71(3) received for EP App. No. 16718006.6 filed on Mar. 4, 2016 on behalf of Probiotical S.P.A. dated Oct. 20, 2020. 27 Pages.
Communication pursuant to Article 94(3) received for EP App. No. 14766538.4 filed on Jul. 17, 2014 on behalf of Probiotical S.P.A. dated Oct. 20, 2017. 6 Pages.
Communication pursuant to Article 94(3) received for EP App. No. 15715813.0 filed on Mar. 5, 2015 on behalf of Probiotical S.P.A. dated Dec. 16, 2020. 4 Pages.
Communication pursuant to Article 94(3) received for EP App. No. 15715813.0 filed on Mar. 5, 2015 on behalf of Probiotical S.P.A. dated Feb. 17, 2020. 5 Pages.
Communication pursuant to Article 94(3) received for EP App. No. 15715813.0 filed on Mar. 5, 2015 on behalf of Probiotical S.P.A. dated Sep. 18, 2018. 7 Pages.
Communication pursuant to Article 71(3) received for EP App. No. 14766538.4 filed on Jul. 17, 2014 on behalf of Probiotical S.P.A. dated May 11, 2018. 45 Pages.
Decision to Grant for Japanese Application No. 2017-502689 dated Jan. 8, 2019 for applicant Probiotical S.P.A. dated Jan. 12, 2021. 4 Pages. (Original + English translation).
Japanese Office Action for Japanese Patent Application No. 2017-546598 on behalf of Probiotical S.P.A. dated Oct. 20, 2020, 7 pages. Japanese +English translation.
Notice of Allowability for U.S. Appl. No. 15/555,920, filed Sep. 5, 2017 on behalf of Probiotical S.P.A. dated Nov. 17, 2020. 5 pages.
Notice of Allowance for U.S. Appl. No. 15/555,920, filed Sep. 5, 2017 on behalf of Probiotical S.P.A. dated Feb. 5, 2021. 8 Pages.
Search Report & Written Opinion for IT MI20131495 filed on Sep. 10, 2013. dated Dec. 12, 2013. 8 Pages.
Search Report & Written Opinion for IT MI20150332 filed on Mar. 5, 2015 on behalf of Probiotical S.P.A. dated Nov. 5, 2015. 9 Pages.
Simmons, J.K. et al. Animal Models of Bone Metastasis. Veterinary Pathology, 2015, vol. 52 (5), 827-841.

* cited by examiner

COMPOSITIONS COMPRISING MELATONIN AND FLAVONOIDS FOR USE IN THE TREATMENT OF TUMOURS RESISTANT TO CHEMOTHERAPY

CROSS-REFERENCE TO RELATED APPLICATIONS

The present application is the U.S. national stage of International Patent Application PCT/162015/000284 filed on Mar. 5, 2015 which, in turn, claims priority to Italian application MI2014A001308 filed on Jul. 17, 2014.

SUMMARY OF THE INVENTION

The present invention relates to compositions comprising at least one flavonoid of natural or synthetic origin in association with melatonin for use to increase the effectiveness of chemotherapeutic treatments used in human and veterinary medicine for the treatment of tumours, in particular for the treatment of tumours resistant to the chemotherapeutic agents currently in use; said at least one flavonoid is selected from the group comprising or, alternatively, consisting of rutin, oxerutin, diosmin and hesperidin, preferably rutin.

BACKGROUND ART

At present, the resistance of tumour cells to chemotherapeutic treatments represents a problem of enormous proportions and in continuous evolution. Drug resistance manifests itself both in solid tumours and in tumours of the lymphatic system, and can occur from the very start of a treatment, or arise subsequently, after an initial positive response to the treatment. Very often, for example, chemoresistance manifests itself during a treatment of relapsing tumours. A even more serious problem is multiple chemoresistance, i.e. the occurrence, after treatment with a given chemotherapeutic agent, of resistance against other chemotherapeutic agents.

The most accredited hypotheses concerning the origin of chemoresistance, which manifests itself in the majority of tumours that initially respond to chemotherapeutic treatment, suggest that drug resistance is the result of a series of mutations at the level of the tumour cells, the ability of tumour cells to "learn" to metabolize the chemotherapeutic agents, repair chemotherapy-induced damage to DNA and prevent chemotherapy-induced apoptosis.

One approach for trying to overcome the problem of chemoresistance is therapy combining different types of chemotherapeutic agents: however, in this case as well, the results are not satisfactory, and indeed multiple resistance against various chemotherapeutic agents occurs with growing and alarming frequency. Notwithstanding research and the continuous development of new drugs, to be used also in combination, the problem of chemoresistance persists and is apparently inevitable, given the malleable nature of cancer cells [Fojo T. and Bates S., Cancer Discov; 3(1); 20-3, 2012].

Consequently, there is a very great need to overcome this problem.

Flavonoids are polyphenolic compounds, secondary metabolites of plants. They are usually present in the plant as glycosides and in the same plant an aglycone can exist in combination with different sugars. Preferably, the flavonoids of the present invention are selected from the group comprising or, alternatively, consisting of rutin, oxerutin, diosmin and hesperidin.

Oxerutin has demonstrated to be useful in favouring elasticity and decreasing capillary permeability, thus favouring a physiological improvement in microcirculation and a reduction in the formation of oedema.

Hesperidin is a glycosylated flavanone, a type of flavonoid that is found above all in citrus fruit. It is particularly abundant in the peel and pulp of such fruit. Its aglycone is called hesperetin. Hesperidin has demonstrated to be a valid vasoprotector and increases the efficiency of collagen and connective tissue.

Diosmin is a semisynthetic molecule (modified starting from a hesperidin molecule), belonging to the family of flavonoids. It is a phlebotropic drug used as a vasoprotector in all pathologies which show a deficiency in the structures of blood vessels, for example in chronic venous insufficiency and acute and chronic haemorrhoidal disease, and as an adjuvant therapy after haemorrhoidectomy.

Rutin, whose chemical name is 2-(3,4-dihydroxyphenyl)-4.5-dihydroxy-3-{3,4,5-trihydroxy-6-[(3,4,5-trihydroxy-6-methyl-oxan-2-yl)oxymethyl]oxan-2-yl]oxy-chromen-7-one, is a flavonoid glycoside consisting of the aglycone quercetin (a flavonol) bonded to the disaccharide rutinose.

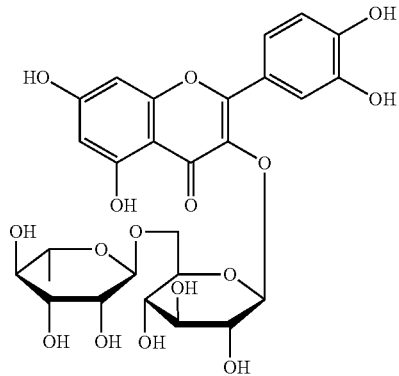

Rutin (commonly also known as rutoside) is found in nature in numerous plants, in particular plants of the genera Citrus and Rheum (rhubarb), in buckwheat, in red wine, in asparagus, in peppermint, in *eucalyptus*, and in many berries such as cranberries (*Vaccinium macrocarpon*) and mulberries.

The reinforcing effect of rutin on the wall of capillaries, and more generally its beneficial action on microcirculation, is exploited for the treatment of haemorrhoids and haematomas.

Recent studies have highlighted the pharmacological properties of rutin, in particular its anti-aggregation activity on platelets [Navarro-Núñez et al. (2008); J. Agric. Food Chem. 56 (9): 2970-6]; its anti-inflammatory activity [Guardia et al. (2001); II Farmaco 56 (9): 683-7; Chan Hun Jung et al. (2007); Arch. Pharmacal Research 30 (12): 1599-1607]; and antioxidant activity [Metodiewa et al. (1997); IUBMB Life 41 (5); 1067], In vitro studies have demonstrated that rutin is capable of inhibiting the vascular endothelial growth factor, thus acting as an angiogenesis inhibitor [Luo et al. (2008); Nutrition and Cancer 60 (6); 800-9].

Recently, Boutogaa et al. [Leukemia Research 35(2011) 1093-1101] described that an extract of *Hammada scoparia*, containing rutin, is capable of inducing apoptosis in adhering leukaemia cells. EP 2 119 434 describes the use of rutin for the treatment of acute myeloid leukaemia, for preventing tumour relapse and/or for preventing the occurrence of solid tumour metastasis. No effects of rutin on tumour cells resistant to chemotherapeutic agents are reported.

WO 200178783 describes anti-tumour compositions comprising quercetin and numerous extracts of medicinal plants, but no reference is made to the activity against chemoresistant cells.

DESCRIPTION OF THE INVENTION

It has indeed been found that compounds selected from the group comprising or, alternatively, consisting of rutin, oxerutin, diosmin and hesperidin in the presence of melatonin re-establish the sensitivity to chemotherapeutic treatment of resistant tumour cell lines, preferably cell lines of breast cancer in women.

Therefore, the present invention relates to a composition comprising a mixture that comprises or, alternatively, consists of: (i) at least one flavonoid, selected from the group comprising or, alternatively, consisting of rutin, oxerutin, diosmin and hesperidin; and (ii) melatonin, for use in the treatment of tumours resistant to chemotherapy, preferably solid tumours and breast cancer in women. Advantageously, said mixture comprises or, alternatively, consists of rutin and melatonin.

The present invention further relates to a composition comprising a mixture which comprises or, alternatively, consists of: (i) at least one flavonoid, selected from the group comprising or, alternatively, consisting of rutin, oxerutin, diosmin and hesperidin; and (ii) melatonin for use as an adjuvant to chemotherapeutic agents for the treatment of tumours resistant to chemotherapy, that is, to increase the effectiveness of chemotherapeutic treatments used in human and veterinary medicine for the treatment of the tumours, preferably solid tumours, in particular in case of resistance to the chemotherapeutic agents currently in use. Advantageously, the use of said composition as an adjuvant makes it possible to reduce the doses used and the daily amount of chemotherapeutic agents to be administered.

The invention also relates to an association of at least one flavonoid, selected from the group comprising or, alternatively, consisting of rutin, oxerutin, diosmin and hesperidin, and melatonin, said association being in a form that is also suitable for the separate or sequential administration of rutin and melatonin.

The present invention further relates to a composition for use in the treatment of chemoresistant tumours comprising a mixture which comprises or, alternatively, consists of: (i) at least one flavonoid selected from the group comprising or, alternatively, consisting of rutin, oxerutin, diosmin and hesperidin; (ii) melatonin; (iii) chemotherapeutic agents; and/or (iv) at least one compound selected from the group comprising or, alternatively, consisting of arctigenin, arctiin, berberine, berbamine, sanguinarine, chelerythrine and *harpagophytum procumbens* (devil's claw, which inhibits the synthesis of PGE2), as such or in the form of plant extracts containing said compounds. Said composition is also for use for increasing the effectiveness of chemotherapeutic treatments used in human and veterinary medicine for the treatment of the tumours, preferably solid tumours, in particular in case of resistance to the chemotherapeutic agents currently in use.

The invention thus also relates to associations of at least one flavonoid selected from the group comprising or, alternatively, consisting of rutin, oxerutin, diosmin and hesperidin, with melatonin and chemotherapeutic agents, said associations being in a form that is also suitable for the separate or sequential administration of the flavonoid, melatonin and chemotherapeutic agents.

Said at least one flavonoid selected from the group comprising or, alternatively, consisting of rutin, oxerutin, diosmin and hesperidin can be used, according to the invention, in association with melatonin and with all known chemotherapeutic agents, said chemotherapeutic agents used either alone or in associations in chemotherapy protocols, in particular for the treatment of solid tumours. Examples of such chemotherapeutic agents comprise or, alternatively, consist of cyclophosphamide, 5-fluoruracyl, methotrexate, platinum complexes (cisplatin, oxaliplatin, carboplatin, etc.), taxanes, doxorubicin, epirubicin and mitoxantrone. In one embodiment, the at least one compound selected from the group comprising or, alternatively, consisting of rutin, oxerutin, diosmin and hesperidin is in association with melatonin and with chemotherapeutic agents which comprise or, alternatively, consist of cyclophosphamide in order to restore or increase sensitivity to chemotherapeutic treatment of resistant tumour cell lines, or for the treatment of tumours, preferably for the treatment of solid tumours.

According to a preferred embodiment, the at least one compound selected from the group comprising or, alternatively, consisting of rutin, oxerutin, diosmin and hesperidin rutin is used in association with melatonin, cyclophosphamide and methotrexate in order to restore or increase sensitivity to chemotherapeutic treatment of resistant tumour cell lines, or for the treatment of the tumours, preferably for the treatment of solid tumours. Preferably, rutin is used in association with melatonin, cyclophosphamide and methotrexate.

A solid tumour consists of a compact mass of tissue which grows and differs from a liquid tumour consisting of cells in suspension. Solid tumours have a specific structure resembling that of a healthy tissue and comprise two mutually dependent portions: the parenchyma and the stroma. In some solid tumours (including those originating from epithelial cells) there is a basal lamina separating the block of tumour cells from the stroma; however, this basal lamina is often incomplete. Though solid tumours represent the majority of human tumours, little is known about the genetic and chromosomal mutations which characterize them; firstly, because it is very difficult to obtain satisfactory chromosomal preparations from malignant tissues and, secondly, because the karyotype of these tumour cells often exhibits strange chromosomes in large numbers. This makes it difficult to distinguish the primary genetic changes from those occurring later, when the tumour phenotype is fully evolving. Despite these difficulties, however, new techniques of cell culture, chromosome banding and hybridization, such as CGH (comparative genomic hybridization), FISH (Fluorescent in situ hybridization) and SKY (Spectral karyotyping) have contributed to a noteworthy increase in the molecular characterizations of cytogenetic anomalies encountered in solid tumours. These techniques have revealed substantial chromosomal rearrangements in tumour cells and the close association among specific chromosomal changes and particular types of solid tumours, above all mesenchymal tumours. Many of the genes involved have been cloned and analyzed, even if our knowledge is still limited. Neoplastic cells are divided into benign and malignant; both types of cells are further divided, according to the tissue of origin, into mesenchymal, epithelial, nervous system, embryonal and germinal tumour cells. Alongside these tumours there are also those of unknown cytologic origin.

According to another aspect of the present invention, the invention relates to compositions comprising: (i) at least one flavonoid selected from the group comprising or, alternatively, consisting of rutin, oxerutin, diosmin and hesperidin; (ii) melatonin; and (iii) at least one chemotherapeutic agent selected from the group comprising or, alternatively, consisting of cyclophosphamide, 5-fluoruracyl, methotrexate, platinum complexes (cisplatin, oxaliplatin, carboplatin, etc.), taxanes, doxorubicin, epirubicin and mitoxantrone; and/or (iv) at least one alkaloid selected from among Berberidaceae, Papavaeraceae and lignans from Asteraceae.

According to another aspect of the present invention, the invention relates to compositions comprising at least one flavonoid, preferably selected from the group comprising or, alternatively, consisting of rutin, oxerutin, diosmin and hesperidin in association with melatonin and at least one compound selected from among Berberidaceae, Papavaeraceae and lignans from Asteraceae.

According to one aspect of the present invention, the invention relates to compositions containing or, alternatively, consisting of an association of alkaloids from Berberidaceae and/or Papavaeraceae, lignans from Asteraceae, and a compound selected from the group comprising or, alternatively, consisting of oxerutin, diosmin, hesperidin and rutin; or else the invention relates to compositions comprising or, alternatively, consisting of an association of alkaloids from Berberidaceae and/or Papavaeraceae, lignans from Asteraceae, a compound selected from the group comprising or, alternatively, consisting of oxerutin, diosmin, hesperidin and rutin, and a compound selected from the group comprising or, alternatively, consisting of natural or synthetic substances, these substances being selected from the group comprising or, alternatively, consisting of apigenin, asparagus (ursolic acid), curcumin, lycopene, chili pepper (capsaicin), resveratrol, green tea (Camellin B) and *Uncaria* sspp.; and/or melatonin; preferably melatonin.

In particular, the compositions of the invention preferably contain the lignans arctigenin and/or arctiin, the alkaloids berberine, and/or berbamine, and/or sanguinarine, and/or chelerythrine, and/or a compound selected from the group comprising or, alternatively, consisting of oxerutin, diosmin, hesperidin and rutin; or else the compositions of the invention preferably contain the lignans arctigenin and/or arctiin, the alkaloids berberine, and/or berbamine, and/or sanguinarine, and/or chelerythrine, and/or a compound selected from the group comprising or, alternatively, consisting of oxerutin, diosmin, hesperidin and rutin and a compound selected from the group comprising or, alternatively, consisting of natural or synthetic substances, these substances being selected from the group comprising or, alternatively, consisting of apigenin, asparagus (ursolic acid), curcumin, lycopene, chili pepper (capsaicin), resveratrol, green tea (Camellin B) and *Uncaria* sspp.; and/or melatonin; preferably melatonin.

According to another aspect of the present invention, the invention relates to compositions comprising or, alternatively, consisting of: (i) at least one flavonoid, preferably selected from the group comprising or, alternatively, consisting of rutin, oxerutin, diosmin and hesperidin; (ii) melatonin; and (iv) at least one alkaloid selected from the group comprising or, alternatively, consisting of arctigenin, arctiin, berberine, berbamine, sanguinarine and chelerythrine and *harpagophytum procumbens* (devil's claw, which inhibits the synthesis of PGE2), as such or in the form of plant extracts containing said compounds.

According to another embodiment, the invention relates to compositions comprising or, alternatively, consisting of: (i) at least one flavonoid, preferably selected from the group comprising or, alternatively, consisting of rutin, oxerutin, diosmin and hesperidin; (ii) melatonin; (iii) at least one chemotherapeutic agent selected from the group comprising or, alternatively, consisting of cyclophosphamide, 5-fluoruracyl, methotrexate, platinum complexes (cisplatin, oxaliplatin, carboplatin, etc.), taxanes, doxorubicin, epirubicin and mitoxantrone; and (iv) at least one alkaloid selected from the group comprising or, alternatively, consisting of arctigenin, arctiin, berberine, berbamine, sanguinarine and chelerythrine and *harpagophytum procumbens* (devil's claw, which inhibits the synthesis of PGE2), as such or in the form of plant extracts containing said compounds. Preferably, the composition comprises rutin, melatonin, cyclophosphamide, methotrexate, arctigenin, arctiin, berberine, berbamine, sanguinarine and chelerythrine.

Preferably, the compositions of the present invention further comprise at least one compound selected from the group comprising or, alternatively, consisting of apigenin, asparagus (ursolic acid), curcumin, lycopene, chili pepper (capsaicin), resveratrol, green tea (Camellin P) and *Uncaria* sspp.

The compositions of the invention are particularly useful for the prevention and/or treatment of neoplasias and for the prevention/suppression of chemoresistance to antiblastics and/or radioresistance to radiotherapy.

The compositions of the invention are particularly useful as adjuvants to chemotherapeutic agents for the treatment of tumours resistant to chemotherapy, preferably solid tumours.

The compositions of the invention are particularly useful for increasing the effectiveness of chemotherapeutic treatments used in human and veterinary medicine for the treatment of the tumours, in particular in case of resistance to the chemotherapeutic agents currently in use.

The applicant has surprisingly found that the composition of the present invention significantly reduces the cell viability of chemoresistant human tumour cells. In particular, the strong anti-inflammatory activity of melatonin enhances the anti-tumour activity of the flavonoids of the present invention, of the association of flavonoids and extracts, and of the association of flavonoids and chemotherapeutic agents. In particular, melatonin contributes to improving sensitivity or reversing the resistance of tumour cells toward conventional chemotherapeutic agents. This multi-targeted therapeutic approach reduces the development of chemoresistant tumour cells and this is also due to the different pharmacological activities of melatonin, which include antioxidant, anti-inflammatory, oncostatic and immunomodulating properties. In addition, given that in the tumour micro-environment inflammatory cells influence the formation of metastases, melatonin acts as an anti-metastatic agent by blocking the ability of tumour cells to invade other remote tissues. In virtue of the above, the compositions of the present invention can be effectively used not only to treat tumours that have already developed chemoresistance, but also to prevent the development of chemoresistance by tumour cells and the formation of metastases.

Therefore, one object of the present patent application is to provide a chemotherapeutic treatment that is more effective in treating chemoresistant tumours than the treatments generally used in medicine, which makes it possible to reduce or even completely eliminate the amount of chemotherapeutic drugs necessary in the treatment of tumours, in particular in the case of chemoresistant tumours, and which can be useful for preventing the development of chemoresistance and the formation of metastases.

Plants belonging to the family of Asteraceae (*Arctium lappa, Cnicus benedictus* and *Saussurea medusa* or other species of *Saussurea*) are characterized by their content of arctigenin and arctiin, molecules already known for their anti-tumour action. The use of extracts of *Arctium lappa* in cancer therapy and prophylaxis is described, for example, in CN 1560265. The use of *Saussurea* as an anti-tumour agent is described, for example, in patent application WO 2006 032380. The anti-tumour activity of lignans extracted from aerial parts of *Saussurea medusa* was described in Cancer Letters, New York, USA, vol. 158, No 1, 1.1.2000, pages 53-59.

Plants belonging to the family of Berberidaceae (*Berberis vulgaris, Berberis aristata*, other species of *Berberis*, and *Mahonia aquifolium*) contain active substances such as berberine and berbamine. The former inhibits chemoresistance and radioresistance, neoangiogenesis and telomerase; it has an anti-hypercholesterolaemic, antidiabetic and cardioprotective effect. However, it has a serious drawback in that it may induce MDR (multidrug resistance). To counter this undesirable effect, it is possible to use berbamine, which, in addition to the cardioprotective effect already mentioned for berberine, shows a specific anti-tumour effect towards MDR and an antiarrhythmic effect. See also the paper published in Alternative and Complementary Therapies, Mary Ann Liebert, Larchmont, New York, USA. Vol 8, No 6, 1.12.2002, pages 336-340, which sums up the knowledge about the use of plants containing berbamine to counter MDR. The cytotoxic effect of the fruit of *Berberis vulgaris* has been described in Int. J. Cancer Res. (Vol 2, No 1, 2006, pages 1-9).

Plants belonging to the family of Papaveraceae (*Eschscholzia californica, Macleaya cordata* or *Bocconia frutescens*) contain chelerythrine and sanguinarine. Chelerythrine has an inhibitory effect on the production of TNF-alpha: this effect, although unsuitable for tumours at an early stage, is however valuable at a pre-terminal and terminal stage, since it suppresses anorexia, cachexia and hyperalgesia, which are typical in pre-terminal and terminal stage oncological patients. Moreover, chelerythrine reduces mitochondrial respiration, which is known to be already poor in the mitochondria of tumour cells. Sanguinarine inhibits both NF-kB and AP-1 [Biochem. Pharmacol. 2004 Sep. 15; 68(6): 1101-11]: both are usually quiescent factors that are activated as a result of exposure to anti-tumour antiblastics or to ionizing radiation. The preparation of anti-tumour extracts of *Macleaya cordata* or *Chelidonium majus* (a plant that is not admitted as a food supplement) containing chelerythrine is described in CN 1470513. The anti-tumour activity of benzophenanthridine alkaloids such as chelerythrine and sanguinarine, and of protoberberine alkaloids such as berberine is also described in Planta Medica, Vol 69(2), 1.2.2003, pages 97-108.

Therefore, the invention relates to compositions containing arctigenin, arctiin, berberine, berbamine, sanguinarine, chelerythrine and rutin in a mixture with suitable excipients.

The active ingredients can be present in a substantially pure and isolated form or in the form of at least three different extracts of plants, one belonging to the family of Asteraceae, one belonging to the family of Berberidaceae and one belonging to the family of Papaveraceae, in addition to rutin.

The plants belonging to the family of Asteraceae are preferably *Arctium lappa, Cnicus benedictus* and *Saussurea medusa*.

The plants belonging to the family of Berberidaceae are preferably *Berberis vulgaris, Berberis aristata* and *Mahonia aquifolium*.

The plants belonging to the family of Papaveraceae are preferably selected from the group comprising *Eschscholzia californica, Macleaya cordata* and *Bocconia frutescens*.

The present invention relates to a composition comprising a mixture which comprises or, alternatively, consists of:
(i) at least one compound selected from the group comprising or, alternatively, consisting of rutin, oxerutin, diosmin and hesperidin; and/or (ii) melatonin; and/or (iv) at least one compound selected from the group comprising or, alternatively, consisting of arctigenin, arctiin, berberine, berbamine, sanguinarine and chelerythrine, as such or in the form of plant extracts containing said compounds; for use in the treatment of neoplasias and the prevention/suppression of chemoresistance to antiblastics and/or radioresistance to radiotherapy. Preferably, the mixture comprises or, alternatively, consists of: (i) at least one flavonoid selected from the group comprising or, alternatively, consisting of rutin, oxerutin, diosmin and hesperidin; (ii) melatonin; and/or (iv) at least one compound selected from the group comprising or, alternatively, consisting of arctigenin, arctiin, berberine, berbamine, sanguinarine and chelerythrine, as such or in the form of plant extracts containing said compounds.

According to a preferred embodiment, the mixture of the present invention comprises or, alternatively, consists of: (i) rutin; (ii) melatonin; and/or (iv) the compounds arctigenin, arctiin, berberine, berbamine, sanguinarine and chelerythrine, as such or in the form of plant extracts containing said compounds.

Preferably, the compositions/mixtures of the present invention further comprise at least one compound selected from the group comprising or, alternatively, consisting of apigenin, asparagus (ursolic acid), curcumin, lycopene, chili pepper (capsaicin), Resveratrol, green tea (Camellin B) and *Uncaria* sspp.

According to a preferred aspect, the compositions/mixtures of the invention, in addition to at least one flavonoid selected from the group comprising or, alternatively, consisting of oxerutin, diosmin, hesperidin and rutin, in association with melatonin, will contain extracts derived from:
a) *Arctium lappa*, in particular from the seeds;
b) *Berberis vulgaris*;
c) *Eschscholzia californica*;

According to a preferred aspect, the extracts derived from each plant belonging to the different families will be present in a proportion comprised between 20% and 600.

The daily doses of the compounds isolated from the extracts will normally be included in the following ranges:
arctigenin and arctiin: 0.1-1.0 g per day
berberine and berbamine: 0.1-1.0 g per day
sanguinarine and chelerythrine: 0.01-0.250 g per day, preferably
0.020-0.150 g per day
rutin: 0.1-0.2 g per day.

According to the invention, the extracts of plants used can be in the form of an oily macerate, alcoholic extract, dry extract (obtained by extraction with ethanol or with methanol or with supercritical $CO_2$), fluid extract or mother tincture.

The compositions of the invention can be used as food supplements, medical devices or pharmaceutical compositions, suitably formulated for oral administration, and will be prepared according to conventional methods well known in the pharmaceutical field, such as those described in "Remington's Pharmaceutical Handbook", Mack Publishing Co., N.Y., USA, using excipients, diluents, filling agents and anti-caking agents that are acceptable for their final use. Examples of forms of administration are soft capsules (sealed, liquid-containing capsules) or semi-rigid or rigid capsules (with a two-part coating, containing powder or granules), pastilles, tablets, wafers, granulates, single-dose sachets of powder, syrups and vials.

In order to improve bioavailability, it is preferable that at least one of the components of the composition be in a micronized form. The micronized compounds are prepared using conventional methods that are well known in the pharmaceutical field. Preferably, in the micronized compounds, the average diameter of the particles is less than 10 µm; more preferably the average diameter of the particles is less than 5 µm and even more preferably it is less than 1 µm.

The invention further relates to the use of an association of arctigenin, arctiin, berberine, berbamine, sanguinarine, chelerythrine, melatonin and at least one flavonoid, preferably selected from the group comprising or, alternatively, consisting of oxerutin, diosmin, hesperidin and rutin for preparing compositions for the treatment of neoplasias and for the prevention/suppression of chemoresistance to antiblastics and/or radioresistance to radiotherapy.

Some embodiments FRn of the present invention are set forth below:

FR1. Rutin for use in the treatment of chemoresistant tumours in association with chemotherapeutic agents and/or with arctigenin, arctiin, berberine, berbamine, sanguinarine, chelerythrine and *harpagophytum procumbens* (devil's claw, which inhibits the synthesis of PGE2), as such or in the form of plant extracts containing said compounds.

FR2. Rutin for use according to FR1, wherein the chemotherapeutic agents are selected from among cyclophosphamide, 5-fluoruracyl, methotrexate, platinum complexes, taxanes, doxorubicin, epirubicin and mitoxantrone.

FR3. Compositions containing arctigenin, arctiin, berberine, berbamine, sanguinarine, chelerythrine and rutin, as such or in the form of plant extracts containing said compounds, in a mixture with suitable excipients.

FR4. Compositions according to FR3, containing extracts derived from:
a) a plant belonging to the family of Asteraceae, selected from the group comprising *Arctium lappa, Cnicus benedictus* and *Saussurea medusa;*
b) a plant belonging to the family of Berberidaceae, selected from the group comprising *Berberis vulgaris, Berberis aristata* and *Mahonia aquifolium;*
c) a plant belonging to the family of Papaveraceae, selected from the group comprising *Eschscholzia californica. Macleaya cordata* or *Bocconia frutescens.*

FR5. Compositions according to FR4, containing extracts derived from:
a) *Arctium lappa;*
b) *Berberis vulgaris;*
c) *Eschscholzia californica.*

FR6. A combination of arctigenin, arctiin, berberine, berbamine, sanguinarine, chelerythrine and rutin, as such or in the form of plant extracts containing said compounds, for use in the treatment of neoplasias and for the prevention/suppression of chemoresistance to antiblastics and/or radioresistance to radiotherapy.

The activity of the association of at least one flavonoid, preferably selected from the group comprising or, alternatively, consisting of oxerutin, diosmin, hesperidin and rutin in association with melatonin and with synthetic chemotherapeutic agents (cyclophosphamide/methotrexate) and/or arctigenin, arctiin, berberine, berbamine, sanguinarine and chelerythrine (indicated with the term "Extracts" in the Tables) was studied in resistant cell lines of adenocarcinomas and carcinomas in comparison with chemosensitive tumour cell lines and line cells.

The present invention relates to a composition comprising a mixture which comprises or, alternatively, consists of: extracts, preferably at a concentration of 450 to 850 ng/ml, for example 650 ng/ml; rutin, preferably at a concentration of 10 µM to 100 µM, for example 20, 30, 40 and 50 µM; cyclophosphamide and/or methotrexate, preferably at a concentration of 500 to 1500 ng/i, preferably 850 ng/ml, 1000 ng/ml, or 1300 ng/ml; and melatonin at a concentration of 0.1 g at 3 g/dose, preferably from 1 to 2 g/dose.

Additional embodiments FRn of the present invention are set forth below:

FRa. Rutin for use in the treatment of chemoresistant tumours in association with:
(i) chemotherapeutic agents, and/or
(ii) arctigenin, arctiin, berberine, berbamine, sanguinarine, chelerythrine and *harpagophytum procumbens* (devil's claw, which inhibits the synthesis of PGE2), as such or in the form of plant extracts containing said compounds, and/or
(iii) a further compound selected from the group comprising or, alternatively, consisting of apigenin, asparagus (ursolic acid), curcumin, lycopene, chili pepper (capsaicin), resveratrol, green tea (Camellin B) and *Uncaria* sspp. or melatonin.

FRb. Rutin for use according to FRa, wherein the chemotherapeutic agents are selected from among cyclophosphamide, 5-fluoruracyl, methotrexate, platinum complexes, taxanes, doxorubicin, epirubicin and mitoxantrone; preferably, it is cyclophosphamide.

FRc. Rutin for use according to FRa, wherein said rutin is in association with:
(i) chemotherapeutic agents selected from the group comprising or, alternatively, consisting of: cyclophosphamide, 5-fluoruracyl, methotrexate, platinum complexes, taxanes, doxorubicin, epirubicin, mitoxantrone; preferably, it is cyclophosphamide; and
(ii) arctigenin, arctiin, berberine, berbamine, sanguinarine and chelerythrine, as such or in the form of plant extracts containing said compounds, and
(iii) a further compound, such as melatonin.

FRd. Compositions for use in the treatment of chemoresistant tumours, wherein said composition contains rutin in accordance with one embodiment, FRa, FRb or FRc.

FRe. Compositions for use according to Frd, said compositions containing arctigenin, arctiin, berberine, berbamine, sanguinarine, chelerythrine and rutin, as such or in the form of plant extracts containing said compounds, in a mixture with suitable excipients.

FRf. Compositions for use according to FRd or FRe, said compositions containing extracts derived from:
d) a plant belonging to the family of Asteraceae selected from the group comprising *Arctium lappa, Cnicus benedictus* and *Saussurea medusa;*
e) a plant belonging to the family of Berberidaceae selected from the group comprising *Berberis vulgaris, Berberis aristata* and *Mahonia aquifolium;*
f) a plant belonging to the family of Papaveraceae selected from the group comprising *Eschscholzia californica. Macleaya cordata* or *Bocconia frutescens.*

FRg. Compositions for use according to FRf, said compositions containing extracts derived from:
a) *Arctium lappa;*
b) *Berberis vulgaris;*
c) *Eschscholzia californica.*

FRh. A combination comprising or, alternatively, consisting of arctigenin, arctiin, berberine, berbamine, sanguinarine, chelerythrine and rutin, as such or in the form of plant extracts containing said compounds; said combination further comprises an additional compound selected from the group comprising or, alternatively, consisting of apigenin, asparagus (ursolic acid), curcumin, lycopene, chili pepper (capsaicin), resveratrol, green tea (Camellin B) and *Uncaria* sspp. or melatonin; preferably melatonin, said combination being for use in the treatment of neoplasias and for the prevention/suppression of chemoresistance to antiblastics and/or radioresistance to radiotherapy.

In particular, chemoresistant human tumour cells MDA-MB-231 (breast adenocarcinoma), ECV-304 (bladder carcinoma), HuH-7 (hepatocellular carcinoma) and HTB-43 (squamous cell carcinoma of the pharynx), chemosensitive tumour cells MCF-7 (breast adenocarcinoma) and non-tumoural healthy human mammal fibroblasts (HMF) were used.

The results, shown in Tables 1-3, demonstrate a directly proportional, though not linear, relationship between the resistance of tumour cells to the chemotherapeutic agent and the effectiveness of the chemotherapeutic agent associated with the extract and/or with rutin.

TABLE 1

| Treatment | Cell viability (%) | | |
|---|---|---|---|
| | MDA-MB-231 | MCF-7 | HMF |
| Control | 100 | 100 | 100 |
| Cyclophosphamide 1300 ng/mL | 89 | 8.6 | 42 |
| Cyclophosphamide 1000 ng/mL | 93 | 7.5 | 48 |
| Cyclophosphamide 850 ng/mL | 96 | 6.9 | 54 |
| Extracts 850 ng/mL | 94 | 5 | 82 |
| Extracts 650 ng/mL | 100 | 8 | 84 |
| Extracts 450 ng/mL | 100 | 12 | 92 |
| Rutin 100 µM | 51 | 4 | 86 |
| Rutin 50 µM | 58 | 5 | 88 |
| Rutin 20 µM | 66 | 8 | 92 |

TABLE 2

| Treatment | Cell viability (%) MDA-MB-231 |
|---|---|
| Extracts 650 ng/mL + Cyclophosphamide 850 ng/mL | 58 |
| Rutin 50 µM + Cyclophosphamide 850 ng/mL | 11 |
| Extracts 650 ng/mL + Rutin 50 µM | 16 |
| Extracts 650 ng/mL + Rutin 50 µM + Cyclophosphamide 850 ng/mL | 3 |

TABLE 3

| Treatment | Cell viability (%) | | |
|---|---|---|---|
| | ECV-304 | HuH-7 | HTB-43 |
| Control | 100 | 100 | 100 |
| Cyclophosphamide 850 ng/mL | 70 | 58 | 36 |
| Extracts 650 ng/mL | 24 | 74 | 24 |
| Rutin 50 µM + Cyclophosphamide 850 ng/mL | 17 | 46 | 21 |
| Extracts 650 ng/mL + Rutin 50 µM + Cyclophosphamide 850 ng/mL | 12 | 32 | 12 |

Table 4 below shows data obtained for MDA-MB-231 cells with quercetin, the aglycone of rutin, alone or in association with cyclophosphamide. The absence of synergistic effects appears evident, unlike what was found with rutin.

TABLE 4

| Treatment | Cell viability (%) MDA-MB-231 |
|---|---|
| Quercetin 100 µM | 76 |
| Quercetin 50 µM | 81 |
| Quercetin 20 µM | 91 |
| Quercetin 100 µM + Cyclophosphamide 850 ng/mL | 62 |
| Quercetin 50 µM + Cyclophosphamide 850 ng/mL | 66 |
| Quercetin 20 µM + Cyclophosphamide 850 ng/mL | 79 |

TABLE 5

The viability of chemoresistant MDA-MB-231 human tumour cells (breast adenocarcinoma) was measured 24, 48 and 72 hours after treatment with the specified compounds. In table 5 the compound cyclo corresponds to cyclophosphamide, whilst the compound metho corresponds to methotrexate.
Test conditions: 5 × 10$^3$ cells; xCELLigence assay

| | Treatment | 24 h | 48 h | 72 h |
|---|---|---|---|---|
| 1 | Control (no treatment) | 100 | 100 | 100 |
| 2 | Rutin (50 µM) + Melatonin (1 mM) | 25.32 ± 1.09 | 10.12 ± 0.85 | 3.25 ± 0.42 |
| 3 | Rutin (20 µM) + Melatonin (10 mM) | 5.46 ± 0.68 | 4.02 ± 0.49 | 3.03 ± 0.29 |
| 4 | Cyclo (20 µM) + Metho (2 µM) + Rutin (50 µM) | 16.18 ± 0.79 | 9.69 ± 0.57 | 4.59 ± 0.77 |
| 5 | Cyclo (20 µM) + Metho (2 µM) + Rutin (50 µM) + Melatonin (1 mM) | 10.70 ± 0.73 | 7.46 ± 0.43 | 4.06 ± 0.49 |
| 6 | Cyclo (10 µM) + Metho (1 µM) + Rutin (50 µM) | 20.73 ± 0.96 | 10.78 ± 0.87 | 6.18 ± 0.47 |
| 7 | Cyclo (10 µM) + Metho (1 µM) + Rutin (50 µM) + Melatonin (1 mM) | 13.59 ± 0.86 | 9.65 ± 0.68 | 5.03 ± 0.75 |

TABLE 5-continued

The viability of chemoresistant MDA-MB-231 human tumour cells (breast adenocarcinoma) was measured 24, 48 and 72 hours after treatment with the specified compounds. In table 5 the compound cyclo corresponds to cyclophosphamide, whilst the compound metho corresponds to methotrexate.
Test conditions: $5 \times 10^3$ cells; xCELLigence assay

| Treatment | 24 h | 48 h | 72 h |
|---|---|---|---|
| 8 Cyclo (20 µM) + Metho (2 µM) + Rutin (20 µM) + Melatonin (10 mM) | 4.58 ± 0.35 | 3.46 ± 0.27 | 2.95 ± 0.38 |
| 9 Cyclo (10 µM) + Metho (1 µM) + Rutin (20 µM) + Melatonin (10 mM) | 4.31 ± 0.56 | 3.35 ± 36.0 | 30.8 ± 0.45 |

TABLE 6

The viability of chemosensitive MCF-7 tumour cells (breast adenocarcinoma) was measured 24, 48 and 72 hours after treatment with the specified compounds. In table 6 the compound cyclo corresponds to cyclophosphamide, whilst the compound metho corresponds to methotrexate.
Test conditions: $5 \times 10^3$ cells xCELLigence assay

| Treatment | 24 h | 48 h | 72 h |
|---|---|---|---|
| Control (no treatment) | 100 | 100 | 100 |
| Cyclo (20 µM) + Metho (2 µM) + Rutin (50 µM) | 12.68 ± 0.61 | 8.24 ± 0.49 | 3.69 ± 0.62 |
| Cyclo (20 µM) + Metho (2 µM) + Rutin (50 µM) + Melatonin (1 mM) | 9.32 ± 0.59 | 6.83 ± 0.68 | 2.67 ± 0.49 |
| Cyclo (10 µM) + Metho (1 µM) + Rutin (50 µM) | 14.43 ± 0.62 | 9.75 ± 0.29 | 4.06 ± 0.38 |
| Cyclo (10 µM) + Metho (1 µM) + Rutin (50 µM) + Melatonin (1 mM) | 10.63 ± 0.73 | 7.04 ± 0.37 | 2.86 ± 0.45 |
| Rutin (50 µM) + Melatonin (1 mM) | 15.59 ± 0.94 | 8.62 ± 0.56 | 3.04 ± 0.45 |
| Rutin (20 µM) + Melatonin (10 mM) | 4.46 ± 0.48 | 3.73 ± 0.38 | 2.64 ± 0.52 |
| Cyclo (20 µM) + Metho (2 µM) + Rutin (20 µM) + Melatonin (10 mM) | 3.79 ± 0.39 | 2.34 ± 0.46 | 2.05 ± 0.24 |
| Cyclo (10 µM) + Metho (1 µM) + Rutin (20 µM) + Melatonin (10 mM) | 4.02 ± 0.46 | 2.79 ± 0.34 | 2.53 ± 0.31 |

The results obtained demonstrate that melatonin enhances the anti-tumour activity of flavonoids. The effect is even more marked if the composition comprises chemotherapeutic agents and/or extracts in addition to melatonin and flavonoids.

Examples of preparation of the extracts used in the invention, as well as examples of compositions of the invention are set forth below.

Example 1—Preparation of an Alcoholic Extract from Fresh Plants 530 grams consisting of the three plants together (each in a proportion of 20% to 60%) are placed in 1100 ml of an ethanol/water mixture (40% to 90% ethanol) and ground in a mixer. The resultant is left to "rest" for a period of 4 to 8 days, with care being taken to ensure that the ground plants remain submerged in the solution. At the end of this period the liquid part is poured off, the vegetable part is pressed and the liquids are collected and then filtered.

The extract thus obtained has a deep green-brownish colour.

Example 2—Preparation of an Alcoholic Extract from Dry Plants

An amount of dry plants comprised from 370 to 450 grams is used for 1200 ml of hydroalcoholic solution (40% to 90% ethanol). The resultant is left to "rest" for about two weeks. At the end of the impregnation/dyeing of the solvent, the liquid part is poured off, the vegetable part is pressed and the liquids are collected and then filtered.

The histogram in FIG. 1 refers to melatonin (M) on MDA-MB-231 cells (24 hours, test conditions: $50 \times 10^3$ cells; xCELLigence assay).

Figure 2:
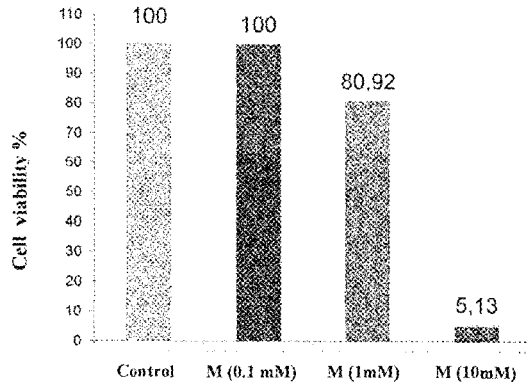

The histogram in FIG. 2 refers to melatonin (M) on MDA-MB-231 cells (48 hours, test conditions: $50 \times 10^3$ cells; xCELLigence assay).

Figure 3:
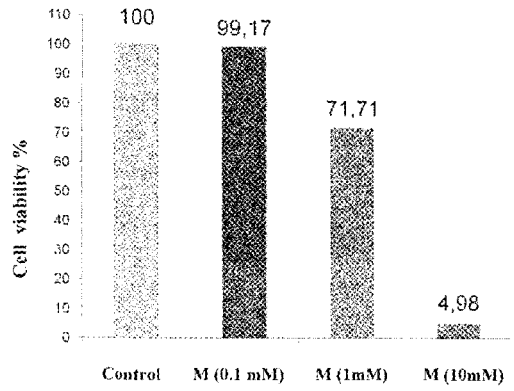

The histogram in FIG. 3 refers to melatonin (M) on MDA-MB-231 cells (72 hours, test conditions: $50 \times 10^3$ cells; xCELLigence assay).

Figure 4:
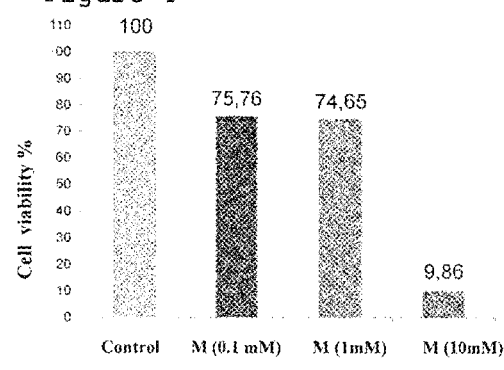

The histogram in FIG. 4 refers to melatonin (M) on MCF-7 cells (24 hours, test conditions: $50 \times 10^3$ cells; xCELLigence assay).

Figure 5:
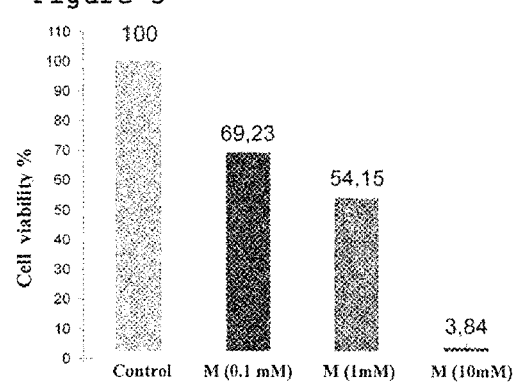

The histogram in FIG. 5 refers to melatonin (M) on MCF-7 cells (48 hours, test conditions: $50 \times 10^3$ cells; xCELLigence assay).

Figure 6:
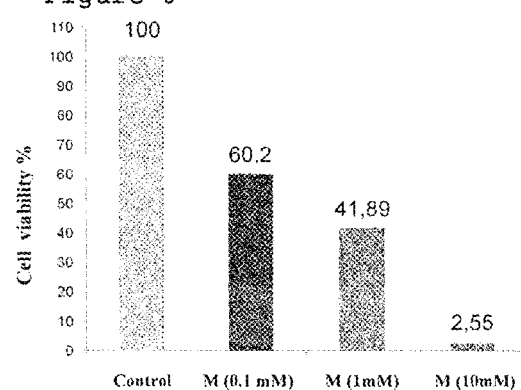

The histogram in FIG. 6 refers to melatonin (M) on MCF-7 cells (72 hours, test conditions: $50 \times 10^3$ cells; xCELLigence assay).

The invention claimed is:

1. A method for treatment of chemoresistant tumours in an individual, the method comprising:
    administering to the individual a mixture comprising in effective amounts therefor:
        (i) rutin at a concentration of at least 20 µM; and
        (ii) melatonin at a concentration of at least 0.1 mM,
    wherein the chemoresistant tumour is breast cancer in woman.

2. The method according to claim 1, wherein said mixture further comprises:
   (iii) at least one chemotherapeutic agent and/or
   (iv) at least one compound selected from the group consisting of arctigenin, arctiine, berberine, berbamine, sanguinarine, chelerythrine and *Harpagophytum procumbens*, in the form of at least one plant extract containing said at least one compound.

3. The method according to claim 2, wherein the at least one chemotherapeutic agent is selected from the group consisting of: cyclophosphamide, 5-fluoruracyl, methotrexate, platinum complexes, taxanes, doxorubicin, epirubicin and mitoxantrone.

4. The method according to claim 3, wherein the component (iv) comprises at least one extract obtained from: a) a plant belonging to the family of Asteraceae, selected from the group consisting of *Arctium lappa, Cnicus benedictus* and *Saussurea medusa*; b) a plant belonging to the family of Berberidaceae, selected from the group consisting of *Berberis vulgaris, Berberis aristata* and *Mahonia aquifolium*; and c) a plant belonging to the family of Papaveraceae, selected from the group consisting of *Eschscholzia californica, Macleaya cordata* and *Bocconia frutescens*.

5. The method according to claim 2, wherein the mixture comprises said at least one extract, the at least one extract obtained from a plant of the group consisting of:
   a) *Arctium lappa;*
   b) *Berberis vulgaris;* and
   c) *Eschscholzia californica.*

6. The method according to claim 2, wherein at least one of the components (i), (ii), (iii) and (iv) is in a micronized form.

7. The method according to claim 2, wherein the chemoresistant tumour is a breast adenocarcinoma.

8. The method according to claim 1, wherein said mixture comprises: (i) rutin, (ii) melatonin and (iii) methotrexate and/or cyclophosphamide.

9. The method according to claim 1, wherein at least one of the components (i) and (ii) is in a micronized form.

10. The method according to claim 9, wherein said mixture further comprises:
    (iii) at least one compound selected from the group consisting of arctigenin, arctiine, berberine, berbamine, sanguinarine, chelerythrine and *Harpagophytum procumbens*, in the form of at least one plant extract containing said at least one compound.

11. The method according to claim 10, wherein at least one of the components (i), (ii) and (iv) is in a micronized form.

12. A method for treatment of neoplasias and for inhibition or suppression of chemoresistance to antiblastics in an individual and/or radioresistance to radiotherapy, the method comprising:
    administering to the individual a mixture comprising in effective amounts therefor:
    (i) rutin at a concentration of at least 20 μM; and
    (ii) melatonin at a concentration of at least 0.1 mM; and optionally further comprising
    (iv) at least one compound selected from the group consisting of arctigenin, arctiine, berberine, berbamine, sanguinarine, chelerythrine and *harpagophytum procumbens*, as such or in the form of plant extracts containing said compounds,
    wherein the neoplasia is a breast cancer in woman.

13. The method according to claim 12, wherein said mixture comprises: (i) rutin; and (ii) melatonin; and optionally further comprising (iv) the compounds arctigenin, arctiine, berberine, berbamine, sanguinarine and chelerythrine, as such or in the form of plant extracts containing said compounds.

14. The method according to claim 13, wherein said mixture further comprises at least one compound selected from the group consisting of: apigenin, ursolic acid optionally obtained from asparagus, curcumin, lycopene, capsaicin optionally obtained from chili pepper, resveratrol, camellin B optionally obtained from green tea, and a compound obtained from *Uncaria* spp.

15. The method according to claim 12, wherein said mixture further comprises at least one compound selected from the group consisting of: apigenin, ursolic acid optionally obtained from asparagus, curcumin, lycopene, capsaicin optionally obtained from chili pepper, resveratrol, camellin B optionally obtained from green tea, and a compound obtained from *Uncaria* spp.

16. The method according to claim 12, wherein the neoplasias is a breast adenocarcinoma.

17. The method according to claim 12, wherein said mixture comprises:
    (iii) at least one compound selected from the group consisting of arctigenin, arctiine, berberine, berbamine, sanguinarine, chelerythrine and *Harpagophytum procumbens*, in the form of at least one plant extract containing said at least one compound.

18. A method of treating metastatic breast cancer, the method comprising:
    administering to an individual an antimetastatic composition comprising in effective amounts therefor:
    (i) rutin at a concentration of at least 20 μM; and
    (ii) melatonin at a concentration of at least 0.1 mM,
    wherein the individual is a woman having metastatic breast cancer.

19. The method of claim 18, said antimetastatic composition further comprising:
    (iii) chemotherapeutic agents and/or
    (iv) at least one compound selected from the group consisting of arctigenin, arctiin, berberine, berbamine, sanguinarine, chelerythrine and *harpagophytum procumbens* in the form of plant extracts containing said compounds.

20. The method according to claim 18, wherein the breast cancer is a breast adenocarcinoma.

* * * * *